(12) United States Patent
Alegria et al.

(10) Patent No.: US 11,807,529 B1
(45) Date of Patent: Nov. 7, 2023

(54) PHOTOSENSITIZED RELEASE OF NITRIC OXIDE

(71) Applicants: Antonio E. Alegria, Trujillo Alto, PR (US); Pedro Sanchez Cruz, Humacao, PR (US)

(72) Inventors: Antonio E. Alegria, Trujillo Alto, PR (US); Pedro Sanchez Cruz, Humacao, PR (US)

(73) Assignee: University of Puerto Rico, San Juan, PR (US)

( * ) Notice: Subject to any disclaimer, the term of this patent is extended or adjusted under 35 U.S.C. 154(b) by 249 days.

(21) Appl. No.: 16/882,709

(22) Filed: May 25, 2020

Related U.S. Application Data

(62) Division of application No. 15/615,510, filed on Jun. 6, 2017, now Pat. No. 10,662,063.

(51) Int. Cl.
*C01B 21/24* (2006.01)
*C07C 243/06* (2006.01)

(52) U.S. Cl.
CPC .................. *C01B 21/24* (2013.01); *C07C 243/06* (2013.01)

(58) Field of Classification Search
None
See application file for complete search history.

(56) References Cited

U.S. PATENT DOCUMENTS

| 6,187,744 | B1* | 2/2001 | Rooney | A61K 31/00 424/718 |
|---|---|---|---|---|
| 2010/0311657 | A1* | 12/2010 | Abuchowski et al. | A61K 47/60 514/13.5 |
| 2011/0166536 | A1* | 7/2011 | Hyde et al. | A61K 33/00 604/304 |
| 2021/0071163 | A1* | 3/2021 | Zhang et al. | C12N 5/0636 |

* cited by examiner

*Primary Examiner* — Sheng H Davis
(74) *Attorney, Agent, or Firm* — Hoglund & Pamias, PSC; Roberto J. Rios

(57) ABSTRACT

The invention proposes the photosensitized generation of nitric oxide (NO) from alanosine (3-(hydroxynitrosoamino)-D,L-alanine) by aluminum phthalocyanine tetrasulfonate (AlPcS4). While NO is obtained in nitrogen-saturated solutions, the invention proposes that both NO and peroxynitrite are produced in air-saturated solutions. Enhancement of NO production occurs in the presence of ubiquinone-0. The invention evidence that NO is produced by the photosensitized oxidation of alanosine. Both NO and peroxynitrite are detected during photoirradiation of AlPcS4 in the presence of 2-methyl-2-nitrosopropane (MNP) and hypoxanthine, but not in the absence of hypoxanthine, in air-saturated solutions, where HX is acting as sacrificial electron donor, thus promoting superoxide formation.

4 Claims, 8 Drawing Sheets

$$\text{Dye} \xrightarrow{h\nu} \text{Dye*} \qquad (1)$$

$$\text{Dye*} + O_2 \longrightarrow \begin{cases} \text{Dye} + {}^1O_2 \text{ (Type II)} & (2) \\ \\ \text{O-Dye} + O_2^{\bullet-} \text{ (Type I)} & (3) \end{cases}$$

$$\text{Dye*} + \text{alanosine} \rightleftharpoons \text{R-Dye} + \text{alanosine}^{\bullet+} \qquad (4)$$

$$\text{R-Dye} + \text{UBQ-0} \longrightarrow \text{Dye} + \text{UBQ-0}^{\bullet-} \qquad (5)$$

$$2\,\text{UBQ-0}^{\bullet-} + 2\,H^+ \longrightarrow \text{UBQ-0} + H_2\text{UBQ-0} \qquad (6)$$

$$\text{alanosine}^{\bullet+} \longrightarrow 2\,NO + \text{other products} \qquad (7)$$

$$O_2^{\bullet-} + NO \longrightarrow ONOO^- \qquad (8)$$

Fig. 2

$$\text{Dye} \xrightarrow{h\nu} \text{Dye}^* \tag{1}$$

$$\text{Dye}^* + O_2 \longrightarrow \begin{cases} \text{Dye} + {}^1O_2 \text{ (Type II)} & (2) \\ \\ \text{O-Dye} + O_2^{\bullet-} \text{ (Type I)} & (3) \end{cases}$$

$$\text{Dye}^* + \text{MNP} \longrightarrow \text{Dye} + \text{NO} + (CH_3)_3C^{\bullet} \tag{8}$$

$$\text{Dye}^* + \text{HX} \longrightarrow \text{R-Dye} + \text{X} \tag{9}$$

$$\text{R-Dye} + O_2 \longrightarrow \text{Dye} + O_2^{\bullet-} \tag{10}$$

$$O_2^{\bullet-} + \text{NO} \longrightarrow \text{ONOO}^- \tag{7}$$

Fig. 3

(a)
(b)
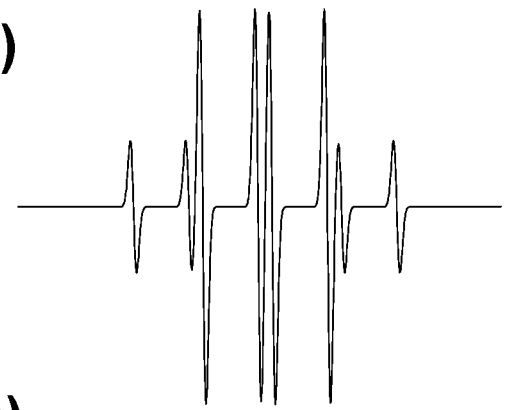
(c)
(d)
Fig. 7

PHOTOSENSITIZED RELEASE OF NITRIC OXIDE

BACKGROUND OF THE INVENTION

Nitric oxide (NO) is an endogenously produced molecule that has multiple roles in physiological processes, including angiogenesis, wound healing, neurotransmission, smooth muscle relaxation, and inflammation. Nitric oxide's action on physiology is highly dependent on location, source, and concentration. It is produced in vivo by NO synthase (NOS). Low nanomolar NO concentrations are produced by eNOS and nNOS to promote vasodilation and neurotransmission, respectively. The iNOS form is capable of producing micromolar levels of NO, often responding to infection and inflammation. In the presence of superoxide (O2•—), NO will react to form peroxynitrite (ONOO—), an even greater oxidant involved in the inflammatory response. Peroxynitrite causes apoptotic or necrotic cell death through nitration of tyrosine residues in proteins, lipid peroxidation, oxidation of critical thiols, DNA strand breaks, NAD depletion and thus energy failure. NO is also a wound healing promoting agent and due to its antibacterial activity, it is a promising agent for reducing implant-associated infections and promoting tissue regeneration in orthopedic procedures.

However, nitric oxide has a short half-life (<1 s) in the presence of oxygen and hemoglobin) in vivo, arising from its high reactivity with transition metals and heme-containing proteins. Due to the reactive nature of gaseous NO, its short half-life, instability during storage, and potential toxicity, including its influence on the systemic blood pressure, chemical strategies for NO storage and release have been developed in an effort to use NO's pharmacological potential. Several ways of NO release to tissues have been developed. Diazeniumdiolates (1-amino-substituted diazen-1-ium-1,2-diolate, i.e. NONOates) and S-nitrosothiols represent the two most diverse NO donor classes. Other classes are organic nitrates and metal nitrosyl compounds such as sodium nitroprusside and potassium nitrosylpentachlororuthenate.

The release of NO from several nanocarriers have been developed to avoid systemic NO side effects while transporting the NO source to the selected tissue. The selective delivery of NO to tissues in adequate concentrations is a developing area of research. These include polymeric nanoparticles, micelles, dendrimers, nanogels, gels, gold nanoparticles, silica nanoparticles and liposomes. The possibility of releasing NO before reaching the tissue site is still a major problem in particle-based systems. In addition, the rate of release of NO at the tissue site using those systems is difficult to be controlled and those where controlled release of NO is observed are mostly metal-based nanoparticle systems containing transition metals with the potential toxicity of those remaining to be tested.

One way of selectively release NO at the needed tissue is to use tissue-penetrating light (wavelengths in the near infrared region, NIR) to activate NO release from molecules. A recent technique, using a 2-photon laser irradiation where NIR photons are added to produce more energetic photons, and NIR-to-visible up-conversion, which are able to release NO from NO-containing molecules and has been developed and used in NO-containing nanoparticles. This technique permits the use of longer, tissue-penetrating wavelengths for the photochemical release of NO at the selected tissue site. The use of liposomes for photodelivering NO from NO-containing chromium complexes has also been reported, where NO is detected outside the liposome. However, a non-tissue-penetrating light wavelength was used. The technical problem to overcome is that those photocontrollable NO donors, where all of them contain transition metals, may exhibit systemic toxicity due to release of transition metal ions. In addition, those systems do not generate peroxynitrite, a species which should enhance the toxic activity of NO.

Cupferron, a carbon-bound diazenium diolate, is able to produce nitric oxide photochemically and upon enzymatic oxidation. A natural product with carbon-bound diazenium diolate structure, without the potential carcinogenicity of cupferron, is alanosine, (FIG. 1). Furthermore, the possibility of generating carcinogenic nitrosamines, as could occur after photolysis of nitrogen-bound diazeniumdiolate ions, has not been reported for carbon-bound diazeniumdiolates. Since other NO-containing compounds release NO by photosensitization, this invention proposes the photosensitized generation of NO from this type of compound. This invention proposes the photosensitized release of NO from alanosine using NIR radiation. Evidence supports the generation of peroxynitrite from air-saturated dye-alanosine solutions and from air-saturated 2-methyl-2-nitrosopropane (MNP) solutions containing a sacrificial electron donor. Although the photosensitized generation of NO from MNP has been reported previously, evidence indicating the photosensitized production of peroxynitrite by MNP in the presence of the sacrificial electron donor, hypoxanthine (HX), is described here. The present invention also used MNP to contrast the behavior of alanosine. The photosensitized production of NO could be used in photodynamic therapies of malignancies, where NO or peroxynitrite are used as toxic agents, and where nanoparticle carriers containing both the NO source and the photosensitizer, are transported to the desired tissue.

BRIEF DESCRIPTION OF THE DAWINGS

Further features and advantages of the invention will become apparent from the following detailed description taken in conjunction with the accompanying figures showing illustrative embodiments of the invention, in which:

FIG. 2 shows the proposed mechanism for the photosensitized oxidation of alanosine and its enhancement by UBQ-0, according to the invention.

FIG. 3 shows the proposed mechanism for the photosensitized release of NO from MNP, according to the invention.

FIG. 7 shows EPR spectra corresponding to irradiated N2-saturated solutions at 670 nm containing 50 mM phosphate buffer (pH 7.4), according to the invention.

DETAILED DESCRIPTION OF THE INVENTION

Materials and Methods

Materials

Figure 1:
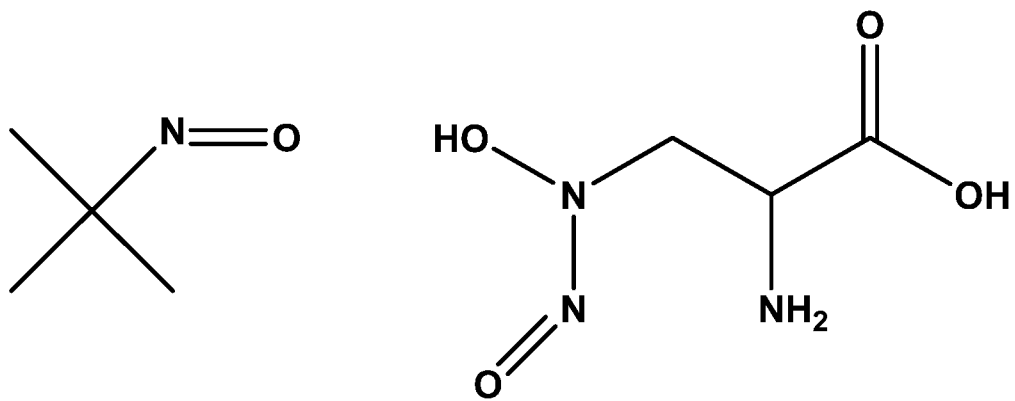
FIG. 1 shows the alanosine and MNP chemical structures.

Alanosine (3-(hydroxynitrosoamino)-D,L-alanine, FIG. 1, was obtained from the NCI DTP Repository (Rockville, MD). The dye aluminum phthalocyanine tetrasulfonate (AlPcS4) was purchased from Frontier Scientific. The compounds ubiquinone-0 (UBQ-0), ferricytochrome c, MNP, HX, L-tyrosine, carboxy-PTIO, superoxide dismutase (SOD, from bovine erythrocytes) and 3-nitrotyrosine were purchased from Sigma- Aldrich Co. All solutions were prepared in phosphate buffer and used the same day. Deionized and Chelex- treated water was used in the preparation of all stock and sample solutions. Chelex treatment of water and buffer was monitored using the ascorbate test, as described by Buettner. Care was always taken to minimize exposure of solutions to light.

Methods

Sample Irradiation for EPR Analysis

The NO probe, carboxy-PTIO, was used to detect NO formation from the production of the carboxy-PTI EPR spectrum, as reported previously. Air- or $N_2$-saturated samples containing AlPcS4 (with absorbance of 1 at 675 nm), alanosine (or MNP, in the presence and absence of HX), in the presence or absence of ubiquinone-0 and carboxy-PTIO in 50 mM phosphate buffer (pH 7.4) were irradiated at 675 nm in a 1 cm light path Pyrex cuvettes with continuous stirring for different periods of time. At the end of each period, samples were then transferred into $N_2$— or air-saturated EPR flat quartz cells (60 X 10 X 0.25 mm) and placed in the EPR instrument cavity for analysis. A 1000 W xenon arc lamp coupled to a Spectral Energy GM 252 high intensity grating monochromator with a bandwidth of ± 20 nm was used as the irradiation source. EPR spectra were recorded on a Bruker ER-200D spectrometer at 100 kHz magnetic field modulation. EPR line intensities were determined from the peak-to-peak derivative amplitudes times the square of the peak-to-peak widths.

Sample Irradiation in the NO Electrode Chamber

Nitric oxide production rates were monitored using a NO-specific electrochemical probe (ISO-NOP) inserted in a thermostated NO chamber (World Precision Instruments, Sarasota, FL) at 37° C. The chamber was either saturated with air or purged with high purity nitrogen followed by injection of 1.00 mL of an air- or nitrogen-saturated solution containing from 0 to 1 mM alanosine or 0 to 3 mM MNP, 10 µM AlPcS4 and 0 or 500 µM UBQ-0 in 50 mM phosphate buffer (pH 7.4). This was followed by immediate exclusion of all gas bubbles out of the sample, through the chamber capillary. The sample was continuously stirred using a spinning bar. Data acquisition was started before irradiation. The sample was then irradiated at 670 nm using a B&W Tek diode laser with a constant power of 255 mW. Basal voltage was calibrated to zero every day. Voltage output corresponding to a 20 µM NO solution was checked every day, and the electrode membrane was replaced in case there was no agreement with previous outputs within 10%. The electrode was calibrated daily with known concentrations of NaNOz by reacting this salt with KI in sulfuric acid medium. NO production data were collected in a computer, and the initial rates of NO consumption (RNO) were measured. RNO values reported are averages of 3 determinations for each type of sample.

Peroxynitrite Formation

Peroxynitrite formation was detected indirectly by its reaction with L-tyrosine to produce 3- nitrotyrosine, as described previously. For this purpose, micromolar amounts of L-tyrosine were included in the air-saturated samples to be irradiated and its nitro-substituted product detected at 274 nm using HPLC. HPLC analyses were performed using a HP Zorbax SB-C18 (4.6 x 250 mm) column and eluted with a solvent mixture of 95 % ammonium acetate (pH 4.7) and 5 % methanol. An Agilent 1100 analytical HPLC system with absorption detection at 276 nm and a flow rate of 0.8 mL/min was used. The retention times of L-tyrosine and 3-nitrotyrosine peaks were determined using commercial standards. All determinations were repeated at least three times, and the average of these determinations is reported.

Superoxide Production

Superoxide production was measured using the SOD-inhibitable ferricytochrome c reduction method, as described elsewhere. Air-saturated solutions containing 0 or 1 mM HX, 10 µM AlPcS4 and 50 µM ferricytochrome C were irradiated at 675 nm for 10 min followed by measuring the solution absorbance at 550 nm. The latter was performed in the presence and absence of 100 U/mL of SOD. Differences in absorbances of irradiated solutions in the presence and absence of SOD correspond to the SOD-inhibitable absorbances. The latter are proportional to the superoxide concentration produced.

Results and Discussion

Photoirradiation of Alanosine-Containing Solutions

Figure 4:
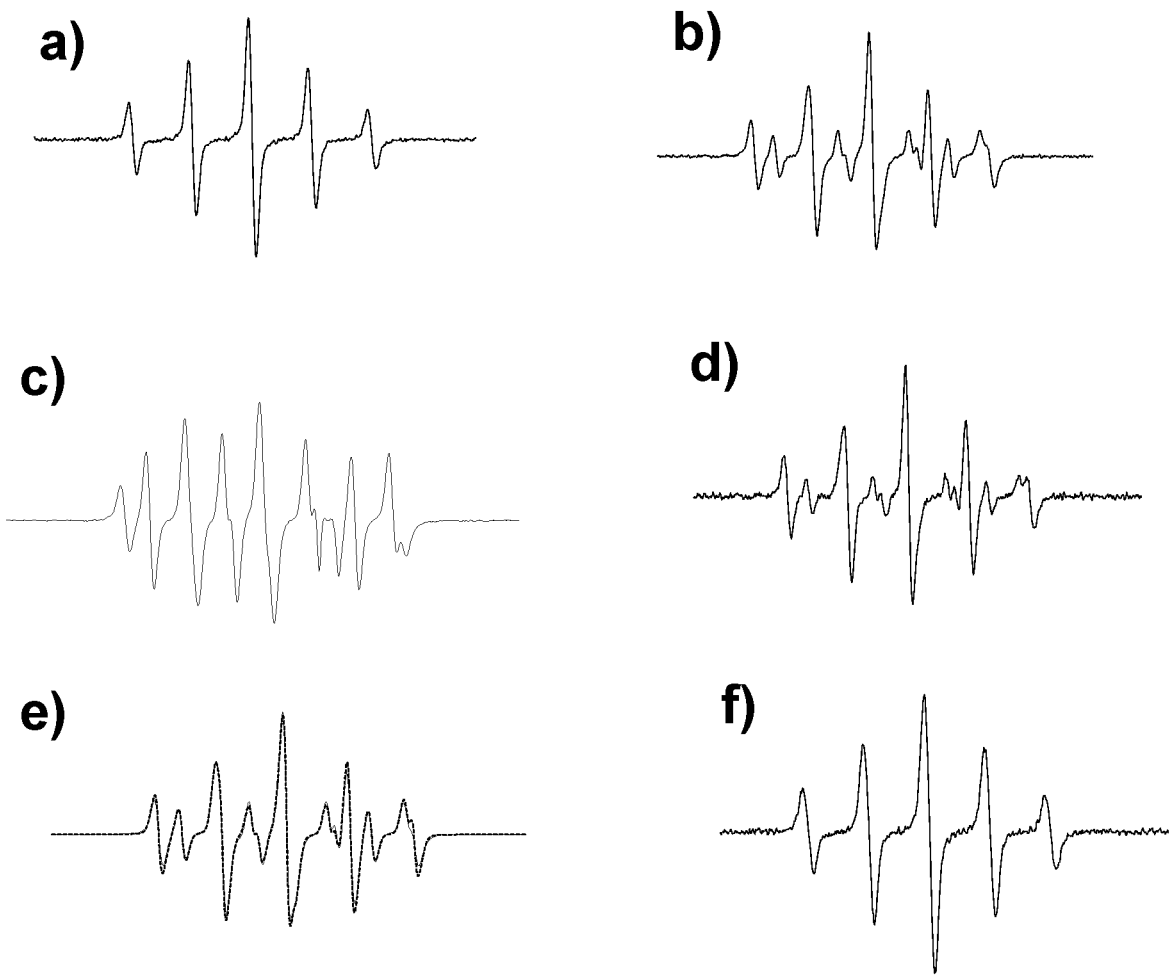
FIG. 4 shows EPR spectra obtained after 15 min irradiation at 675 nm of samples containing 0 or 1 mM alanosine, 0 or 10 µM AlPcS4, 500 µM carboxy-PTIO in 50 mM phosphate buffer (pH 7.4), according to the invention.
Figure 5:
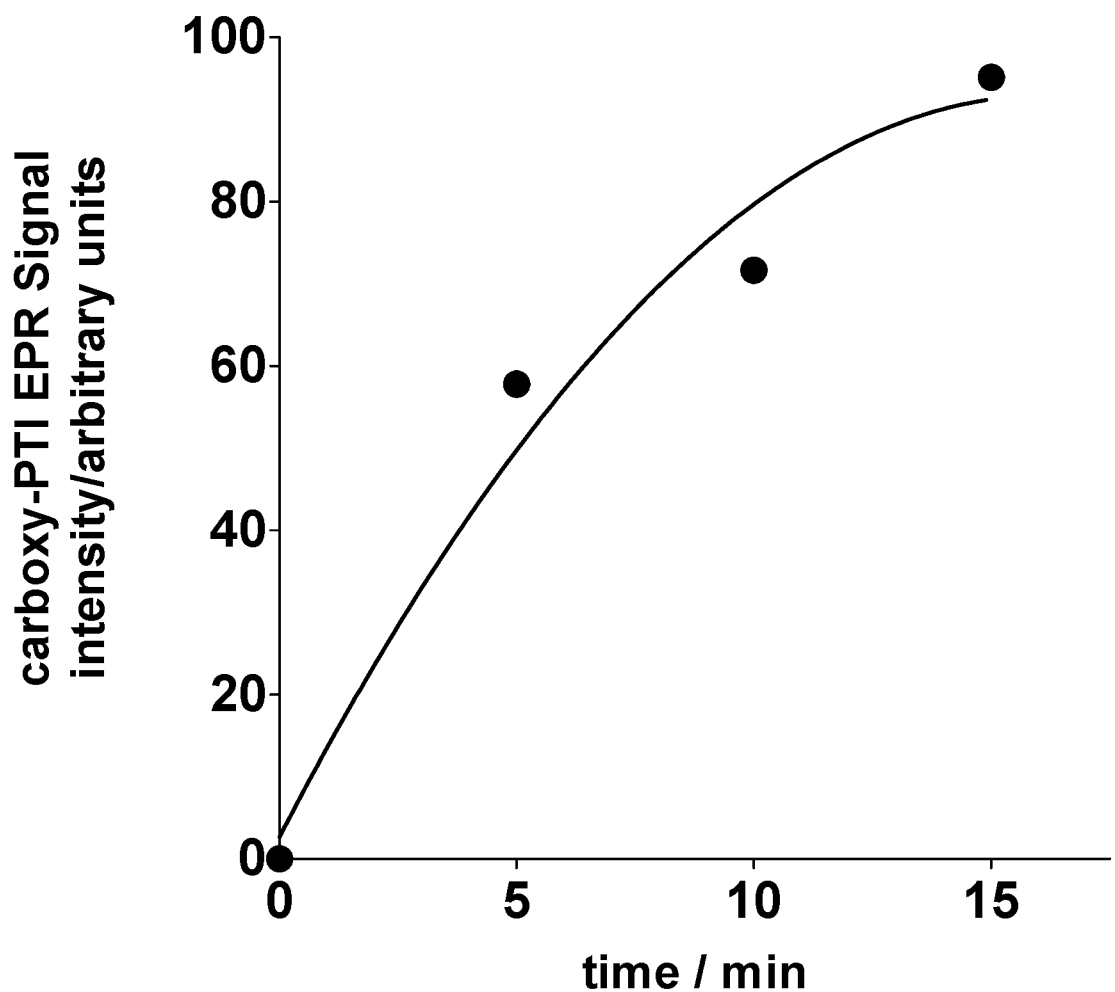
FIG. 5 shows a plot indicating the increase in the lowest-field EPR peak intensity of carboxy-PTI with irradiation time at 675 nm of a N2-saturated sample containing 500 µM carboxy-PTIO, 500 µM alanosine, AlPcS4 (A=1) and 50 mM phosphate buffer (pH=7.4), according to the invention.

Photoirradiation, at 675 nm, of a Nz-saturated sample, containing 4 mM carboxy-PTIO, 10 µM AlPcS4, 500 µM alanosine and 50 mM phosphate buffer (pH 7.4) produces the NO-derived carboxy-PTI EPR spectrum, as shown in FIG. 4b, indicating the photosensitized production of NO. Carboxy-PTIO and carboxy-PTI spectra are characterized by splitting constants aN (2Ns) = 8.10 G and g value = 2.0062 for carboxy-PTIO and aN (IN) = 9.8 G, aN (IN) = 4.4 G and g value = 2.0059 for carboxy-PTI, in agreement with previously reported values. The lowest field EPR peak of carboxy-PTI increases in intensity as a function of irradiation time as shown in FIG. 5 which illustrates the increase in the lowest-field EPR peak intensity of carboxy-PTI with irradiation time at 675 nm of a Nz-saturated sample containing 500 µM carboxy-PTIO, 500 µM alanosine, AlPcS4 (A=1) and 50 mM phosphate buffer (pH=7.4). If an identical sample is saturated with air, a smaller intensity of the lowest-field carboxy-PTI EPR peak is detected as compared to that corresponding to the Nz-saturated sample, after 15 min of irradiation, as shown in FIG. 4d vs FIG. 4b. This indicates that oxygen is competing against alanosine in reacting with the dye excited state. Since aziridinylquinones enhance the photosensitized oxidation of HX (30) by, presumably, inhibiting back electron transfer from the reduced dye to the HX cation, we tested if UBQ-0 presents a similar behavior in the present system by enhancing alanosine photosensitized oxidation. In fact, addition of 500 µM UBQ-0 to an air-saturated solution of alanosine with the same composition as described above increases the intensity ratio of the lowest-field EPR peak of carboxy-PTI to that of the lowest-field EPR peak of carboxy-PTIO by a factor of 2, as shown in FIG. 4d vs. FIG. 4e. An increase by a factor of ca. 3.5 in the same ratio of peak intensities is detected, upon 500 µM UBQ-0 addition, in $N_2$-saturated solutions, as shown in FIG. 4b vs FIG. 4c. The larger increase in carboxy-PTI production upon UBQ-0 addition under $N_2$— vs air- saturated conditions should be due to the absence of oxygen competition for both the excited and reduced dye in Nz-saturated solutions. No carboxy-PTI is observed in the absence of alanosine or dye, (FIGS. 4a and 4f). These observations indicate that a photosensitized oxidation of alanosine is occurring as explained below. FIGS. 4a-f are EPR spectra obtained after 15 min irradiation at 675 nm of samples containing 0 or 1 mM alanosine, 0 or 10 µM AlPcS4, 500 µM carboxy-PTIO in 50 mM phosphate buffer (pH 7.4). Specific additional conditions of each sample are: (4a) 0 mM alanosine, 10 µM AlPcS4, N2-saturated; (4b) 1 mM alanosine, 10 µM AlPcS4, N2-saturated sample; (4c) 1 mM alanosine, 10 µM AlPcS4, N2-saturated sample + 500 µM UBQ- 0; (4d) 1 mM alanosine, 10 µM AlPcS4, air-saturated sample; (4e) 1 mM alanosine, 10 µM AlPcS4, air- saturated sample + 500 µM UBQ-0; (4f) 1 mM alanosine, 0 µM AlPcS4, N2-saturated sample. Dotted-line spectrum in (4e) corresponds to a spectral simulation and optimization using WINSIM with parameters stated above.

Figure 6:
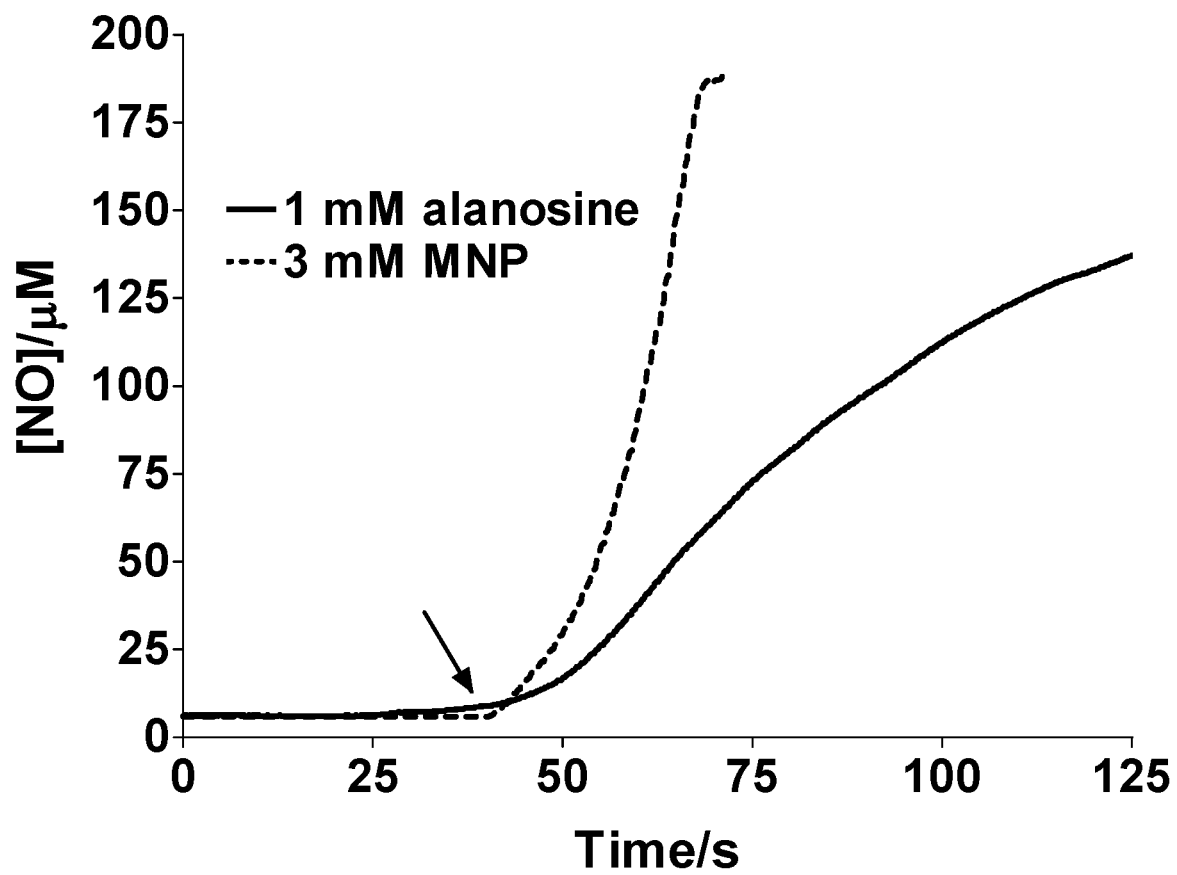
FIG. 6 shows a plot indicating NO traces after illumination at 670 nm of N2-saturated samples containing 1 mM alanosine or 3 mM MNP in the presence of 10 µM AlPcS4 and 50 mM phosphate buffer (pH 7.4) at 37° C., according to the invention.

Further evidence for the photosensitized production of NO was obtained by the photoirradiation of a solution containing 1 mM alanosine, 10 µM AlPcS4 and 50 mM phosphate buffer (pH 7.4) under air- or $N_2$— saturated conditions at the NO electrode chamber, as shown in FIG. 6 which indicates NO traces after illumination at 670 nm of Nz-saturated samples containing 1 mM alanosine or 3 mM MNP in the presence of 10 µM AlPcS4 and 50 mM phosphate buffer (pH 7.4) at 37° C., the arrow indicates the instance illumination is started. Again, rates of NO formation are smaller in air- as compared to $N_2$-saturated conditions, as shown in Table 1 below, indicating initial rates of NO formation, RNO, under several conditions, in irradiated samples at 675 nm containing 1.0 mM alanosine or 3.0 mM MNP, 10 µM AlPcS4, 50 mM phosphate buffer (pH 7.4) and the stated conditions. Errors are the standard deviations of the average of 3 determinations and the last column indicates the ratio of RNO in the presence of UBQ-0 to that in its absence. Furthermore, addition of 500 µM UBQ-0 to air-saturated or $N_2$-saturated solutions increases the rate of NO formation by ca. 12.3 and ca. 3.3, respectively, as shown in Table 1 below. Evidence that electrons are being provided to UBQ-0, via the reduced species of the dye, by alanosine oxidation, is the appearance of the semiquinone of UBQ-0 in Nz-saturated solutions and only when both dye and alanosine are present in the irradiated sample, as shown in FIG. 7 where Epr spectra is shown corresponding to irradiated N2-saturated solutions at 670 nm containing 50 mM phosphate buffer (pH 7.4), (a) 10 µM AlPcS4, 1 mM alanosine and 500 µM UBQ-0, (c) 10 µM AlPcS4, 0 mM alanosine and 500 µM UBQ-0, (d) 0 µM AlPcS4, 1 mM alanosine and 500 µM UBQ-0. Spectrum (b) is a spectral simulation and optimization using WINSIM. Hyperfine coupling constants are aH(3Hs) = 2.44 G, aH(1H) = 1.95 G and aH(6Hs) = 0.03 G, which agree with previously reported values.

FIG. 2 depicts a possible mechanism supported by this observation, where UBQ-0 accepts the electrons from the reduced dye (reaction (5) followed by (6)), thus inhibiting back-electron transfer (reverse of reaction (4)). The proposed mechanism for the photosensitized oxidation of alanosine and its enhancement by UBQ-0 is explained in FIG. 2, where HzUBQ-0 is the ubiquinone hydroquinone; the dye is a tetraanionic species; the species R-Dye and O-Dye represents reduced and oxidized species of the dye, respectively. Thus, the fact that UBQ-0 is accepting electrons from the reduced dye could explain while UBQ-0 increases NO production in the case of alanosine-containing samples. Since MNP photosensitized oxidation is not the pathway for NO release from MNP, UBQ-0 addition in MNP-containing solutions has no such dramatic effect on the rate or extent on the photosensitized NO release from MNP.

TABLE 1

| NO source | $N_2$-saturated | air-saturated | RNO ($n$M/s) | RNO+$_{UBQ}$/RNO-$_{UBQ}$ |
|---|---|---|---|---|
| alanosine | X | | 2.03 ± 0.03 | 3.3 |
| | + 500 µM UBQ-0 | | 6.8 ± 0.2 | |
| | | X | 0.12 ± 0.03 | 12.3 |
| | | + 500 µM UBQ-0 | 1.47 ± 0.04 | |
| MNP | X | | 2.4 ± 0.2 | 1.2 |
| | + 500 µM UBQ-0 | | 2.8 ± 0.1 | |
| | | X | 0.51 ± 0.05 | 1.3 |
| | | + 500 µM UBQ-0 | 0.67 ± 0.04 | |

Figure 8:
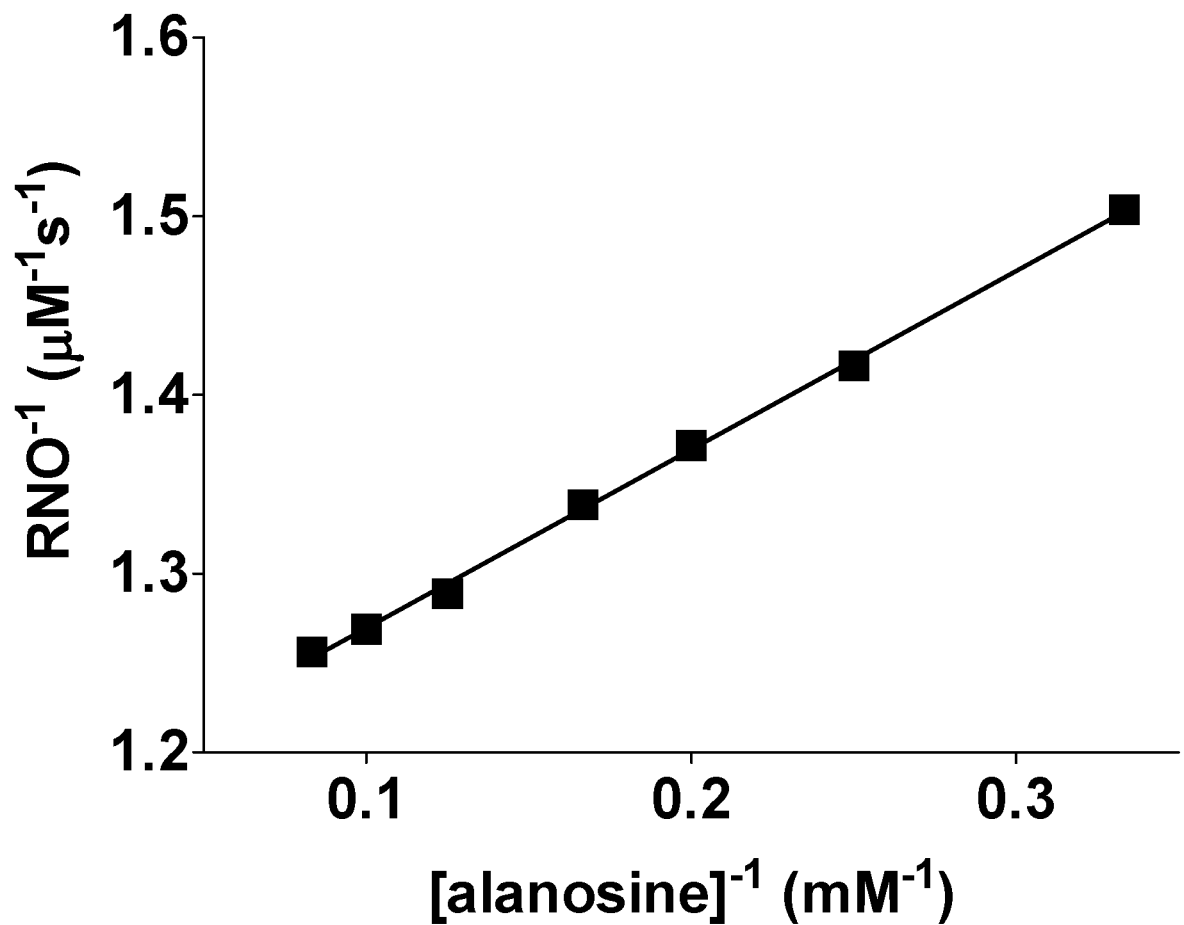
FIG. 8 shows a plot indicating the determination of $k_4$ for alanosine, according to the invention.

The bimolecular rate constant for the reaction of alanosine with the excited sensitizer ($k_4$, see FIG. 2) is a measure of the ability of the sensitizer to produce NO from alanosine and can be determined as described previously, assuming a competition between alanosine and Oz in colliding with the excited dye in air-saturated solutions. If the initial rate of NO formation in air-saturated solutions at a given alanosine concentration (RNO) is measured and compared to the limiting initial rate at saturating alanosine concentration (RNO)$_{max}$, the following equation is obeyed:

$$\frac{1}{RNO} = \frac{k_{O_2}[O_2]}{k_4[alanosine](RNO_{max})} + \frac{1}{RNO_{max}} \quad (1)$$

where $k_{o2}$ and $k_4$ are the bimolecular rate constants between the excited state of AlPcS4 and $O_2$ and alanosine, respectively. The rate constant, $k_{o2}$, when the dye is AlPcS4 has been reported as 1.8 x $10^9$ $M^{-1}$ $s^{-1}$. Thus, the bimolecular rate constant $k_4$ can be determined from the slope of the plot of 1/RNO vs. 1/[alanosine], as shown in FIG. 8 where the determination of $k_4$ for alanosine is indicated. Air saturated samples containing 10 µM AlPcS4, alanosine in 50 mM phosphate buffer (pH 7.4) were irradiated at 670 nm in the NO electrode chamber and initial NO rates were determined from the NO traces. From the slope and intercept of that graph, the concentration of oxygen and $k_{o2}$, a value of $k_4 = (4.2 ± 0.3)$ x $10^8$ $M^{-1}$ $s^{-1}$ is obtained.

Photosensitized Peroxynitrite Production in Alanosine-Containing Solutions

Photoirradiation of an air-saturated sample containing 10 µM AlPcS4, 2.0 mM alanosine, 100 µM tyrosine and 50 mM phosphate buffer (pH 7.4) produces 3-nitrotyrosine, as identified by HPLC using a commercial standard, as shown in Table 2 below indicating the amounts of 3-nitrotyrosine obtained after photolysis at 675 nm of air-saturated samples containing AlPcS4 (A=1 at 675 nm), alanosine or MNP, 100 µM L-tyrosine and 50 mM phosphate buffer (pH 7.4). Errors are the standard deviations of the average of 3 determinations. The latter is indirect evidence for peroxynitrite formation as previously described. Thus, the reaction of the photosensitized generation of superoxide ($O_2$.—) with NO produces the powerful oxidant and nitrating agent, peroxynitrite (ONOO—). Since alanosine is being photooxidized by the dye-excited state, the reduced dye is able to reduce triplet oxygen to the superoxide ion, followed by peroxynitrite formation as explained below.

TABLE 2

| NO source | Irradiation time/min | [HX] / mM | [3-nitrotyrosine]/ µM |
|---|---|---|---|
| 2 mM alanosine | 10 | 0 | 5 ± 1 |
|  | 15 | 0 | 11 ± 2 |
|  | 20 | 0 | 16 ± 3 |
| 2 mM MNP | 10 | 1 | 0 |
|  | 15 | 1 | 0 |
|  | 25 | 1 | 0.5 ± 0.1 |

Photoirradiation of MNP-Containing Solutions

The photosensitized release of NO by MNP solutions in the presence of AlPcS4 has been previously reported and reproduced here, as indicated in FIG. 6. Energy transfer from the triplet state of AlPcS4 to the triplet state of MNP was postulated to lead to the enhanced homolytic decomposition of MNP to generate NO and the tert-butyl radical. In the present invention, no 3-nitrotyrosine formation was detected in air-saturated samples containing MNP and AlPcS4, even after 25 minutes of irradiation. In a previous work, we observed that a sacrificial electron donor such as HX enhances the photosensitized reduction of an electron acceptor such as an alkylating quinone, via HX photosensitized oxidation. Thus, we propose in the present invention that addition of HX to an air-saturated MNP-containing solution should enhance oxygen reduction with the consequent production of superoxide and, therefore, peroxynitrite should be detected. In fact, if HX is added to MNP + AlPcS4 solutions, 3-nitrotyrosine is detected after 25 minutes of irradiation although in much smaller amounts than that detected for alanosine + AlPcS4 solutions at an even shorter period of irradiation, and with identical MNP and dye concentrations as those used in alanosine-containing solutions, as shown in Table 2. That HX enhances the photosensitized production of superoxide is proven by our measurement of the SOD-inhibitable reduction of ferricytochrome C. Addition of 1.0 mM HX to an air-saturated solution containing 10 µM AlPcS4 and 50 µM ferricytochrome C in 50 mM phosphate buffer (pH 7.4), which was irradiated for 10 minutes at 670 nm, produces an increase by a factor of 29 (0.058 ± 0.002 vs 0.020 ± 0.001) in the SOD-inhibitable absorbance at 550 nm. Thus, HX is providing the electrons for the increase in superoxide production, and thus in peroxynitrite formation as demonstrated in FIG. 3 which illustrates the proposed mechanism for the photosensitized release of NO from MNP, where X is xanthine; the dye is a tetraanionic species; the species R-Dye and O-Dye represents reduced and oxidized species of the dye, respectively.

In contrast to alanosine, addition of UBQ-0 to MNP-containing solutions has no significant effect on the extent of the photosensitized NO production, (Table 1), since the mechanism of NO release by MNP is not oxidation, as previously reported.

Conclusion

The photosensitized production of NO from alanosine occurs under aerobic and anaerobic conditions. While the presence of UBQ-0 increases the rate of photosensitized NO production by alanosine, it has little influence on the rate of photosensitized production of NO by MNP. These observations indicate that NO is produced by the photosensitized oxidation of alanosine. In air-saturated solutions, AlPcS4 photosensitize the production of peroxynitrite from alanosine while the photosensitized production of peroxynitrite from MNP requires the presence of HX as sacrificial electron donor. This invention demonstrates that a carbon-bound diazenium diolate such as alanosine can be photosensitized to produce both NO and peroxynitrite. The photosensitized production of NO could be used in photodynamic therapies of malignancies where NO or peroxynitrite are used as the toxic agents and where nanoparticle carriers, containing both the NO source and the photosensitizer, are transported to the desired tissue.

Although the present invention has been described herein with reference to the foregoing exemplary embodiment, this embodiment does not serve to limit the scope of the present invention. Accordingly, those skilled in the art to which the present invention pertains will appreciate that various modifications and equivalents are possible, without departing from the technical spirit of the present invention.

The invention claimed is:

1. A method of photosensitized production of Nitride Oxide (NO) comprising:
   photoirradiating a solution containing 2-methyl-2-nitrosopropane (MNP) and aluminum phthalocyanine tetrasulfonate (AlPcS4) in the presence of a sacrificial electron donor compound, wherein Nitride Oxide (NO) is produced.

2. The method of claim 1, wherein said sacrificial electron donor compound is hypoxanthine (HX).

3. The method of claim 1, wherein peroxynitrite is also produced.

4. The method of claim 1, wherein said solution is either air-saturated or N2-saturated.

* * * * *